(12) United States Patent
Liang et al.

(10) Patent No.: US 10,160,712 B2
(45) Date of Patent: Dec. 25, 2018

(54) METHOD OF CATALYTIC OXIDATION OF LIGNITE USING OXYGEN AS OXIDANT AT ATMOSPHERIC PRESSURE

(71) Applicant: CHINA UNIVERSITY OF MINING AND TECHNOLOGY, Jiangsu (CN)

(72) Inventors: Jing Liang, Jiangsu (CN); Huihui Yang, Jiangsu (CN); Xianyong Wei, Jiangsu (CN); Zhimin Zong, Jiangsu (CN)

(73) Assignee: CHINA UNIVERSITY OF MINING AND TECHNOLOGY, Jiangsu (CN)

( * ) Notice: Subject to any disclaimer, the term of this patent is extended or adjusted under 35 U.S.C. 154(b) by 0 days.

(21) Appl. No.: 15/548,100

(22) PCT Filed: Dec. 7, 2016

(86) PCT No.: PCT/CN2016/108846
§ 371 (c)(1),
(2) Date: Aug. 2, 2017

(87) PCT Pub. No.: WO2017/206468
PCT Pub. Date: Dec. 7, 2017

(65) Prior Publication Data
US 2018/0237371 A1   Aug. 23, 2018

(30) Foreign Application Priority Data
Jun. 1, 2016 (CN) .......................... 2016 1 03835223

(51) Int. Cl.
| | |
|---|---|
| C07C 51/21 | (2006.01) |
| C07C 65/21 | (2006.01) |
| C07C 55/02 | (2006.01) |
| C07C 55/14 | (2006.01) |
| C07C 57/03 | (2006.01) |
| C07C 59/01 | (2006.01) |
| C07C 59/08 | (2006.01) |
| C07C 63/06 | (2006.01) |
| C07C 63/307 | (2006.01) |
| B01J 31/04 | (2006.01) |
| B01J 31/02 | (2006.01) |

(52) U.S. Cl.
CPC ........... *C07C 51/21* (2013.01); *B01J 31/0237* (2013.01); *B01J 31/0247* (2013.01); *B01J 31/0249* (2013.01); *B01J 31/04* (2013.01); *C07C 55/02* (2013.01); *C07C 55/14* (2013.01); *C07C 57/03* (2013.01); *C07C 59/01* (2013.01); *C07C 59/08* (2013.01); *C07C 63/06* (2013.01); *C07C 63/307* (2013.01); *C07C 65/21* (2013.01); *B01J 2231/70* (2013.01)

(58) Field of Classification Search
CPC .... C07C 51/21; B01J 31/0247; B01J 2231/70
See application file for complete search history.

(56) References Cited

U.S. PATENT DOCUMENTS

| | | | |
|---|---|---|---|
| 4,368,333 A | 1/1983 | Kovacs et al. | |
| 4,792,620 A * | 12/1988 | Paulik ............... | B01J 31/0231 560/232 |

FOREIGN PATENT DOCUMENTS

| | | | |
|---|---|---|---|
| CN | 103319324 | 9/2013 | |
| CN | 106008193 | 10/2016 | |
| EP | 1459804 A1 * | 9/2004 | .......... B01J 31/0249 |

OTHER PUBLICATIONS

Norskov et al, Nature Chemistry, Towards the Computational Design of Solid Catalysts, 2009, 1, pp. 37-46. (Year: 2009).*
Yang et al, Fuel, Catalytic Oxidation of Lignite to Carboxylic Acids by Molecular Oxygen in an Aqueous FeCl3 Solution, 2017, 202, pp. 129-134. (Year: 2017).*
Hayashi et al., "Evaluation of Macromolecular Structure of a Brown Coal by Means of Oxidative Degradation in Aqueous Phase," Energy & Fuels, Jan. 1999, pp. 69-76.

* cited by examiner

*Primary Examiner* — Paul A Zucker
(74) *Attorney, Agent, or Firm* — JCIPRNET

(57) ABSTRACT

A method of catalytic oxidation of a lignite using oxygen as an oxidant at atmospheric pressure is provided. The method includes the following steps, pulverizing the lignite to 200-mesh or less; drying the pulverized lignite at a temperature of 80° C. in vacuum for 10 h; weighing 0.5 g of the dried lignite and sequentially adding 10 ml of acetic acid, 0.5 mmol of a catalyst and 0.15-0.25 mmol of a cocatalyst into a round-bottom flask filled with the oxygen, keeping oxygen pressure at 0.1 MPa, reacting at a temperature of 80-120° C. for 4-12 h; using oxygen as the oxidant to catalytically oxidize the reacted lignite at an atmospheric pressure of 0.1 MPa; filtering after the reaction is finished; decompressing the filtrate to remove the acetic acid, adding a small amount of ethyl acetate to dissolve, and using an excess $CH_2N_2$/ether solution to esterify for 10 h at room temperature; and analyzing the esterified product through a gas chromatography-mass spectrometer.

2 Claims, 1 Drawing Sheet

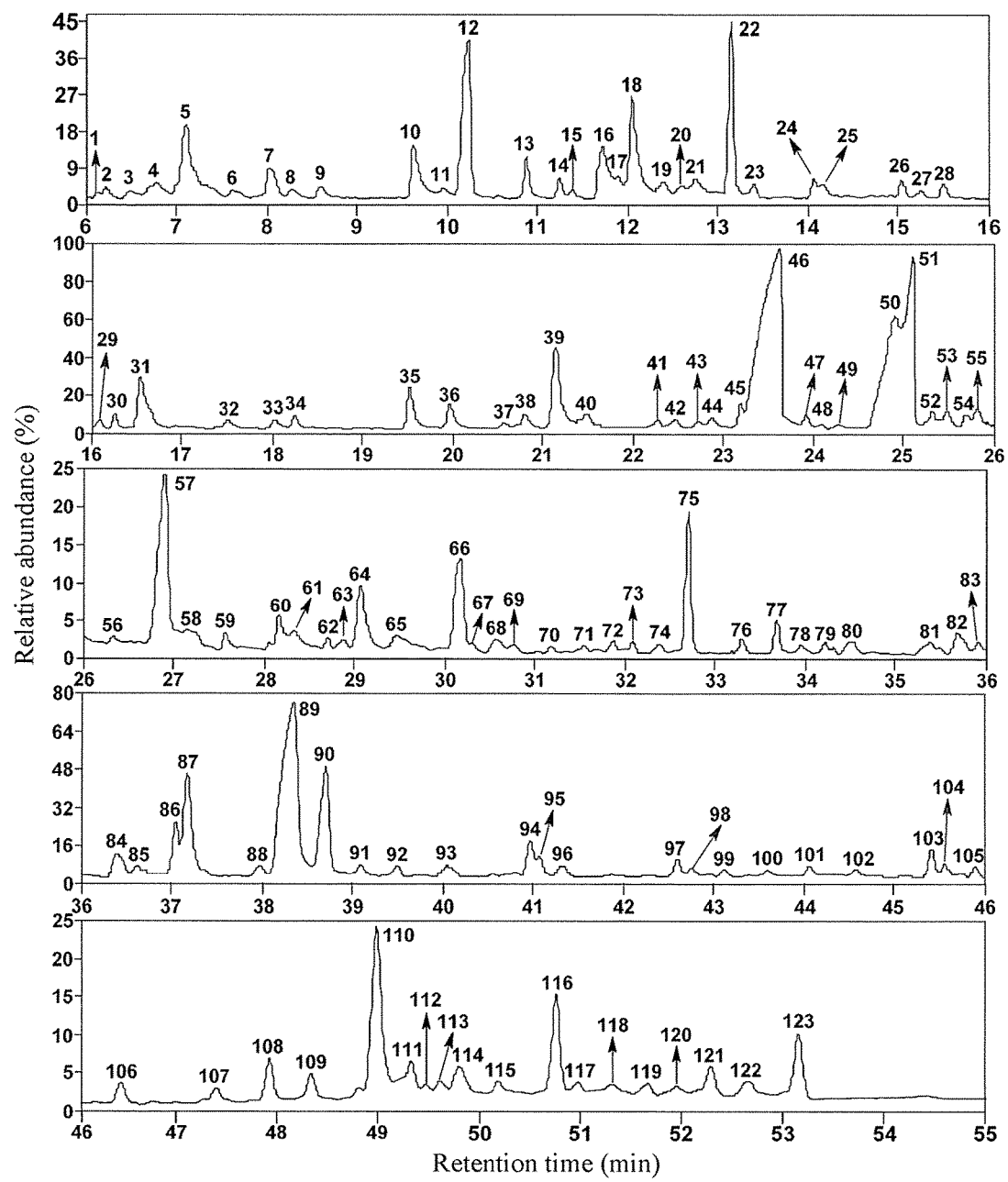

METHOD OF CATALYTIC OXIDATION OF LIGNITE USING OXYGEN AS OXIDANT AT ATMOSPHERIC PRESSURE

CROSS-REFERENCE TO RELATED APPLICATION

This application is a 371 application of International PCT application serial no. PCT/CN2016/108846, filed on Dec. 7, 2016, which claims the priority benefit of Chinese application no. 201610383522.3, filed on Jun. 1, 2016. The entirety of each of the above-mentioned patent applications is hereby incorporated by reference herein and made a part of this specification.

TECHNICAL FIELD

The present invention relates to a method of mild oxidation of lignite, and especially relates to a method of catalytic oxidation of lignite using oxygen as an oxidant at atmospheric pressure.

RELATED ART

China's lignite is rich in resources, accounting for about 13% of the total coal reserves. But the lignite has low degree of coalification, has the shortcomings of high content of water, high ash content, low calorific value and the like, has low thermal efficiency obtained by direct combustion, will bring serious environmental pollution, and is considered as inferior fuel, and therefore it needs some new technologies to utilize the lignite limitedly with high value-added. Through an oxidation reaction, the coal can be used as a raw material to obtain high value-added products on the one hand, and a structure possibly existing in coal can be deducted by identifying the product structure on the other hand. The oxidation method of coal according to oxidants can be divided into a hydrogen peroxide oxidation method, an oxidative acid oxidation method, an oxygen (air) alkali oxidation method, a ruthenium tetroxide oxidation method, a sodium hypochlorite oxidation method and the like.

Further, the air/oxygen oxidation method of the coal is mostly studied in many oxidation methods, mainly because air or oxygen is cheap and easy to obtain, and the yield of organic acid in products is higher.

Kamiya et al. studied the oxidation reaction in an $O_2/Na_2CO_3$ system and an $O_2/K_2CO_3$ system by using Japanese bituminous coal as a raw material. The reaction temperature was set at 250-280° C., the oxidation time was 120 minutes, and the initial pressure of oxygen was 3 MPa; after the reaction was finished, coal cinder is filtered out, and acidified with sulfuric acid, regenerated humic acid was filtered out, and a filtrate was extracted with 2-butanone. The experimental results showed that the product yield was obviously affected by oxidation temperature, alkali amount and stirring speed, and the reaction conditions for the highest yield of coal acid were as follows: the reaction temperature was 270° C., a ratio of coal to $Na_2CO_3$ was equal to 1:3, the initial pressure of oxygen was 1.5 MPa, the stirring speed was 85 r/min, the reaction time was 2 h, and the yield of coal acid reached 65%.

Y. Kamiya et al. firstly adopted thermal treatment and then carried out alkali-oxygen oxidation in order to improve the yield of benzene carboxylic acid. The temperature of thermal treatment was 300-500° C. The experimental results showed that the yield of benzene carboxylic acid of Australian lignite subjected to thermal treatment was improved to a certain extent, and the highest yield could be increased to 30%.

Pan Qikun et al. carried out a series of experiments such as the production of benzene carboxylic acid by alkali oxidation of lignite and production of p-phthalic acid by reforming of benzene carboxylic acid. By using Huolinhe lignite as a raw material, they investigated the effects of various reaction conditions on the yield of coal acid to obtain the optimum reaction conditions as follows: the reaction temperature was 240° C., the initial pressure of oxygen was 5.5 MPa, a ratio of alkali to coal was 3:1, the reaction time was 0.5 h, and the yield of obtained coal acid was 35.2%, wherein the yield of benzene polycarboxylic acid reached 22.52%.

It can be seen from the above that the reaction conditions selected by different researchers during alkali-O2 oxidation change in a narrow range, the selected alkali is $Na_2CO_3$, NaOH and KOH, the oxidant is cheap air or $O_2$, the temperature range is between 220° C.-300° C., and pressure is often at 3 to 10 MPa, the obtained product includes mainly benzene polycarboxylic acid, in addition, there are various small molecular fatty acids in a solution, including formic acid, oxalic acid, acetic acid, malonic acid, pyruvic acid and the like. The alkali-oxygen oxidation method requires high temperature and high pressure conditions, and needs a large amount of alkali, so that the practical use of the method has been restricted by these shortcomings.

SUMMARY OF THE INVENTION

An object of the present invention is to provide a cheap, environment-friendly, mild and efficient method of catalytic oxidation of lignite using oxygen as an oxidant at atmospheric pressure.

The object of the present invention is realized as follows: the method is used to mildly oxidize the lignite using the oxygen as the oxidant under the action of a N-hydroxy amide catalyst and a metal salt or metal oxide cocatalyst;

The specific process comprises the following steps: pulverizing the lignite to 200 meshes or less, drying a pulverized coal sample at a temperature of 80° C. in vacuum for 10 h, weighing 0.5 g of the treated coal sample, sequentially adding 10 ml of acetic acid, 0.5 mmol of a catalyst, and 0.15-0.25 mmol of a cocatalyst into a round-bottom flask, connecting a tee joint to an upper orifice of a condenser pipe, replacing oxygen in vacuum for three times so that the round-bottom flask is filled with oxygen, keeping the oxygen pressure at 0.1 MPa, reacting at a temperature of 80° C.-120° C. for 4-12 h, observing the reaction conditions; using the oxygen as the oxidant to catalytically oxidize the lignite at atmospheric pressure of 0.1 MPa; filtering after the reaction is finished; decompressing a filtrate to remove the acetic acid, adding a small amount of ethyl acetate to dissolve, then using an excess $CH_2N_2$/ether solution to esterify for 10 h at room temperature, using a 0.45 μm filter paper to filter, and analyzing an esterified product through a gas chromatography-mass spectrometer (GC/MS).

The gas chromatography conditions are as follows: helium is used as a carrier gas, the flow rate is 1.0 mL/min, and the split ratio is 20:1; the injection port temperature is 280° C.; the temperature raising procedure is as follows: the initial temperature is 70° C., and is raised at 20° C./min to 280° C., and kept for 1 min, and the running time is 14.5 min; the mass spectrography conditions are as follows: the ion source temperature is 280° C., the transmission line temperature is 280° C., and the detection range of relative molecular mass is 50-650 amu.

The catalyst is a N-hydroxy amide catalyst, and the N-hydroxy amide catalyst is one of N-hydroxy o-sulfonyl benzimide, N,N-dihydroxy pyromellitic diimide, 1,3,5-trihydroxyisocyanuric acid, N-hydroxy-N-methylbenzamide, 3,5-dinitro-N-hydroxy-N-methylbenzamide, and 1-hydroxy-2,2-diphenyl-3-indolone; the structure of the catalyst is as follows:

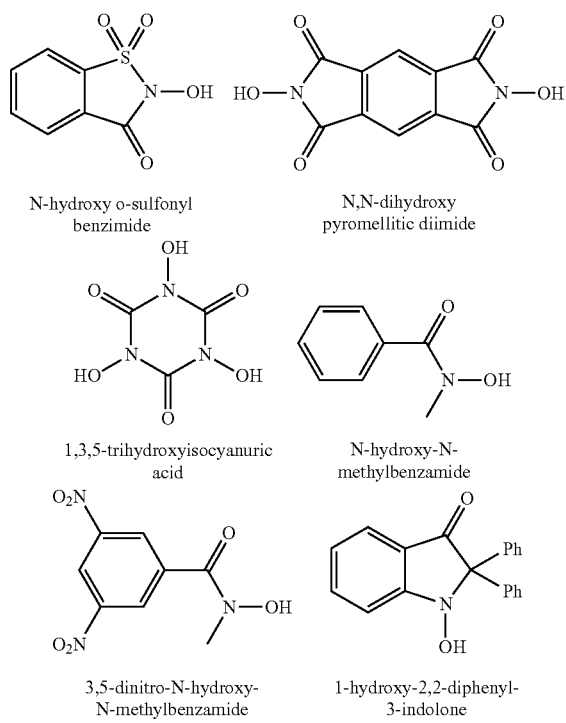

The cocatalyst is a metal salt or metal oxide, and the metal salt or metal oxide is one of cobalt acetate, manganese acetate, copper acetate, iron acetate, and manganese dioxide.

When the lignite is 0.5 g, the amount of the catalyst is 0.5 mmol, the molar ratio of the cocatalyst is 30%-50% based on the catalyst, and the total yield of coal acid is 66.21%-85.47%, wherein the yield of benzene carboxylic acid reaches 22.58%-28.85%.

The method has the following beneficial effects that with the above-mentioned scheme, the cheap and environment-friendly oxygen is used as the oxidant, the N-hydroxy amide compound is used as the catalyst, the metal salt or metal oxide is used as the cocatalyst, and for oxidation products of the lignite, a total of 123 kinds of compounds are identified through GC/MS, including 40 kinds of monocarboxylic acid compounds (MCAs), 14 kinds of dicarboxylic acid compounds (DCAs), 4 kinds of tricarboxylic acid compounds (ATCAs), 21 kinds of benzene carboxylic acid compounds (BCAs), 23 kinds of hydrocarbon alkyl compounds (HCs), 15 kinds of other compounds (OCs) and 6 kinds of heteroatomic compounds.

The content of monocarboxylic acid compounds (MCAs) is larger in oxidation products, the content is up to 28.34%-36.08%, the content of 7-carbonyl octanoic acid is the highest, and the contents of other compounds such as 3-hydroxypropionic acid, 2-hydroxyacetic acid, 2-hydroxypropionic acid, nonane acid, 2-ethyl-3-carbonyl butyric acid and (Z)-octadeca-11-enoic acid are also higher.

The dicarboxylic acid in the oxidation products mainly includes short chains, the longest chain hydrocarbon is undecanedioic acid, compounds without substituents, such as glutaric acid, suberic acid and adipic acid, and dicarboxylic acid compounds with substituents, such as methyl glutaric acid, hydroxy-succinic acid and methyl adipic acid are detected through GC/MS. The total content of diacid compounds is 10.26%-18.34%, and the relative content of 2,4-dimethyl adipic acid is the highest, followed by maleic acid, succinic acid and 2-hydroxysuccinic acid.

The total content of tricarboxylic acid in the oxidation products is 3.15%-7.82%, including 4 kinds of tricarboxylic acid compounds such as 1,2,3-propanetricarboxylic acid, 1,3,5-pentanetricarboxylic acid, 2-hydroxy-1,3,5-pentanetricarboxylic acid, and 1,3,6-hexanetricarboxylic acid, wherein the relative content of 1,3,6-hexanetricarboxylic acid is the highest.

A total of 21 kinds of benzene carboxylic acid compounds are generated in the oxidation products, and the total content reaches 22.58%-28.85%, including 3 kinds of tricarboxylic acid compounds, 1 kind of dicarboxylic acid compound, and 17 kinds of monocarboxylic acid compounds; it can be seen that more kinds of benzene monocarboxylic acid compounds are generated, and the content of benzene-1,3,5-tricarboxylic acid is the highest, followed by benzoic acid, 4-methoxy benzoic acid and benzene-1,2,4-tricarboxylic acid.

Compared with the tradition alkali-O$_2$ oxidation method, the method provided by the present invention has the substantial characteristics that: although the oxygen is used as the oxidant, the reaction conditions are mild, the lignite can be mildly and efficiently oxidized at atmospheric pressure (the oxygen pressure is kept at 0.1 MPa) under the middle temperature (80-120° C.) condition, use of high-temperature and high-pressure equipment is avoided, and the energy consumption is reduced; the oxidation efficiency is high, and the total yield of coal acid reaches 66.21%-85.47%, wherein the yield of benzene carboxylic acid reaches 22.58%-28.85%; the lignite oxidation method is mild and efficient.

A total of 123 compounds are identified by analyzing and detecting the distribution of oxidation products through an Agilent 7890/5975 gas chromatography-mass spectrometer, including 40 kinds of monocarboxylic acid compounds (MCAs) with the total content of 28.34%-36.08%, 14 kinds of dicarboxylic acid compounds (DCAs) with the total content of 10.26%-18.34%, 4 kinds of tricarboxylic acid compounds (ATCAs) with the total content of 3.15%-7.82%, 21 kinds of benzene carboxylic acid compounds (BCAs) with the total content of 22.58%-28.85%, 23 kinds of hydrocarbon alkyl compounds (HCs) with the total content of 7.62%-25.20%, 15 kinds of other compounds (OCs) with the total content of 5.05%-13.98%, and 6 kinds of heteroatomic compounds with the total content of 0.98%-2.53%, wherein the total yield of coal acid reaches 66.21%-85.47%, and the yield of benzene carboxylic acid reaches 22.58%28.85%.

The method has the following advantages that:

1. The reaction is a catalytic oxidation process, and the amounts of the catalyst and the cocatalyst are few; when the amount of lignite is 0.5 g, the amount of the catalyst is 0.5 mmol, and the amount of the cocatalyst is 0.15-0.25 mmol.

2. The reaction conditions are mild, the reaction is carried out at atmospheric pressure (0.1 MPa) and a middle temperature (80-120° C.), the requirements on equipment are low, the defect that the oxygen needs to be used to oxidize under high-temperature and high-pressure conditions is overcome, and the energy consumption is reduced.

3. The reaction has high efficiency, and the total yield of coal acid reaches 66.21%-85.47%, wherein the yield of benzene carboxylic acid reaches 22.58%-28.85%; compared with the traditional alkali-$O_2$ oxidation method, the yields of coal acid and benzene carboxylic acid are higher, and this catalytic oxidation system not only has a better oxidation effect on an aromatic side chain, but also has a better oxidation effect on a chain hydrocarbon material from the aspect of the oxidation products.

BRIEF DESCRIPTION OF THE DRAWINGS

The drawing is a total ion flow chromatogram of oxidation products of a lignite according to the present invention.

DETAILED DESCRIPTION

The method is used to mildly oxidize a lignite using oxygen as an oxidant under an action of a N-hydroxy amide catalyst and a metal salt or metal oxide cocatalyst;

The specific process comprises the following steps: pulverizing the lignite to 200 meshes or less, drying a pulverized coal sample at a temperature of 80° C. in vacuum for 10 h, weighing 0.5 g of the treated coal sample, sequentially adding 10 ml of acetic acid, 0.5 mmol of a catalyst and 0.15-0.25 mmol of a cocatalyst into a round-bottom flask, connecting a tee joint to an upper orifice of a condenser pipe, replacing oxygen in vacuum for three times so that the round-bottom flask is filled with oxygen, keeping the oxygen pressure at 0.1 MPa, reacting at a temperature of 80° C.-120° C. for 4-12 h, and observing the reaction conditions; using the oxygen as the oxidant to catalytically oxidize the lignite at atmospheric pressure of 0.1 MPa; filtering after the reaction is finished; decompressing a filtrate to remove the acetic acid, adding a small amount of ethyl acetate to dissolve, then using an excess $CH_2N_2$/ether solution to esterify for 10 h at room temperature, using 0.45 μm filter paper to filter, and analyzing an esterified product through a gas chromatography-mass spectrometer GC/MS.

The gas chromatography conditions are as follows: helium is used as a carrier gas, the flow rate is 1.0 mL/min, and the split ratio is 20:1; the injection port temperature is 280° C.; the temperature raising procedure is as follows: the initial temperature is 70° C., and is raised at 20° C./min to 280° C., and kept for 1 min, and the running time is 14.5 min; the mass spectrography conditions are as follows: the ion source temperature is 280° C., the transmission line temperature is 280° C., and the detection range of relative molecular mass is 50-650 amu.

The catalyst is a N-hydroxy amide catalyst, and the N-hydroxy amide catalyst is one of N-hydroxyo-sulfonyl benzimide, N,N-dihydroxy pyromellitic diimide, 1,3,5-trihydroxyisocyanuric acid, N-hydroxy-N-methylbenzamide, 3,5-dinitro-N-hydroxy-N-methylbenzamide and 1-hydroxy-2,2-diphenyl-3-indolone;

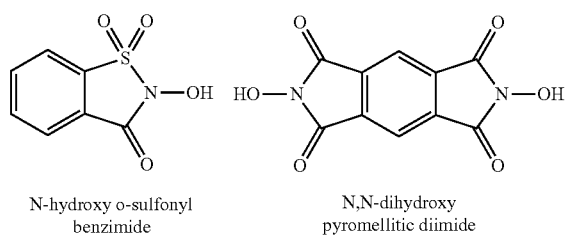

N-hydroxy o-sulfonyl benzimide

N,N-dihydroxy pyromellitic diimide

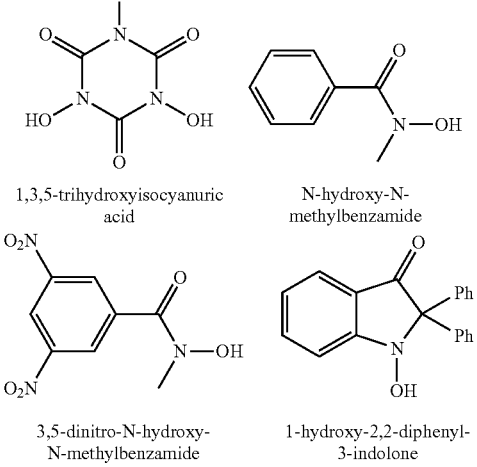

1,3,5-trihydroxyisocyanuric acid

N-hydroxy-N-methylbenzamide 3,5-dinitro-N-hydroxy-N-methylbenzamide 1-hydroxy-2,2-diphenyl-3-indolone The cocatalyst is a metal salt or metal oxide, and the metal salt or metal oxide is one of cobalt acetate, manganese acetate, copper acetate, iron acetate and manganese dioxide.

The lignite is 0.5 g, the amount of the catalyst is 0.5 mmol, the molar ratio of the cocatalyst is 30%-50% based on the catalyst, and the total yield of coal acid is 66.21%-85.47%, wherein the yield of benzene carboxylic acid reaches 22.58%-28.85%.

Embodiment 1

The process comprises the following steps: pulverizing Shengli lignite to 200 meshes or less, drying a pulverized coal sample at a temperature of 80° C. in vacuum for 10 h, weighing 0.5 g of the treated coal sample, sequentially adding 10 ml of acetic acid, 0.5 mmol of N-hydroxy o-sulfonyl benzimide and 0.15 mmol of manganese acetate into a round-bottom flask, connecting a tee joint to an upper orifice of a condenser pipe, replacing oxygen in vacuum for three times so that the round-bottom flask is filled with the oxygen, keeping the oxygen pressure at 0.1 MPa, reacting at a temperature of 120° C. for 4 h, and observing the reaction conditions; filtering after the reaction is finished; decompressing a filtrate to remove the acetic acid, adding a small amount of ethyl acetate to dissolve, then adding an excess $CH_2N_2$/ether solution to esterify at room temperature for 10 h, using 0.45 μm filter paper to filter, and analyzing an esterified product through GC/MS.

A total of 123 compounds are identified by analyzing and detecting the distribution of oxidation products through an Agilent 7890/5975 gas chromatography-mass spectrometer, including 40 kinds of monocarboxylic acid compounds (MCAs) with the total content of 28.34%, 14 kinds of dicarboxylic acid compounds (DCAs) with the total content of 11.68%, 4 kinds of tricarboxylic acid compounds (ATCAs) with the total content of 7.82%, 21 kinds of benzene carboxylic acid compounds (BCAs) with the total content of 24.35%, 23 kinds of hydrocarbon alkyl compounds (HCs) with the total content of 11.75%, 15 kinds of other compounds (OCs) with the total content of 13.98%, and 6 kinds of heteroatomic compounds with the total content of 2.08%, and the total yield of coal acid reaches 72.19%, wherein the yield of benzene carboxylic acid reaches 24.35%.

Embodiment 2

The process comprises the following steps: pulverizing Shengli lignite to 200 meshes or less, drying a pulverized coal sample at a temperature of 80° C. in vacuum for 10 h, weighing 0.5 g of the treated coal sample, sequentially adding 10 ml of acetic acid, 0.5 mmol of N, N-dihydroxy pyromellitic diimide and 0.20 mmol of copper acetate into a round-bottom flask, connecting a tee joint to an upper orifice of a condenser pipe, replacing oxygen in vacuum for three times so that the round-bottom flask is filled with the oxygen, keeping the oxygen pressure at 0.1 MPa, reacting at a temperature of 80° C. for 12 h, and observing the reaction conditions; filtering after the reaction is finished; decompressing a filtrate to remove the acetic acid, adding a small amount of ethyl acetate to dissolve, then adding an excess $CH_2N_2$/ether solution to esterify at room temperature for 10 h, using 0.45 μm filter paper to filter, and analyzing an esterified product through GC/MS.

A total of 123 compounds are identified by analyzing and detecting the distribution of oxidation products through an Agilent 7890/5975 gas chromatography-mass spectrometer, including 40 kinds of monocarboxylic acid compounds (MCAs) with the total content of 30.22%, 14 kinds of dicarboxylic acid compounds (DCAs) with the total content of 10.26%, 4 kinds of tricarboxylic acid compounds (ATCAs) with the total content of 3.15%, 21 kinds of benzene carboxylic acid compounds (BCAs) with the total content of 22.58%, 23 kinds of hydrocarbon alkyl compounds (HCs) with the total content of 25.20%, 15 kinds of other compounds (OCs) with the total content of 7.61%, and 6 kinds of heteroatomic compounds with the total content of 0.98%, and the total yield of coal acid reaches 66.21%, wherein the yield of benzene carboxylic acid reaches 22.58%.

Embodiment 3

The process comprises the following steps: pulverizing Shengli lignite to 200 meshes or less, drying a pulverized coal sample at a temperature of 80° C. in vacuum for 10 h, weighing 0.5 g of the treated coal sample, sequentially adding 10 ml of acetic acid, 0.5 mmol of 1,3,5-trihydroxyisocyanuric acid and 0.25 mmol of manganese dioxide into a round-bottom flask, connecting a tee joint to an upper orifice of a condenser pipe, replacing oxygen in vacuum for three times so that the round-bottom flask is filled with the oxygen, keeping the oxygen pressure at 0.1 MPa, reacting at a temperature of 100° C. for 10 h, and observing the reaction conditions; filtering after the reaction is finished; decompressing a filtrate to remove the acetic acid, adding a small amount of ethyl acetate to dissolve, then adding an excess $CH_2N_2$/ether solution to esterify at room temperature for 10 h, using 0.45 μm filter paper to filter, and analyzing an esterified product through GC/MS.

A total of 123 compounds are identified by analyzing and detecting the distribution of oxidation products through an Agilent 7890/5975 gas chromatography-mass spectrometer, including 40 kinds of monocarboxylic acid compounds (MCAs) with the total content of 32.25%, 14 kinds of dicarboxylic acid compounds (DCAs) with the total content of 13.46%, 4 kinds of tricarboxylic acid compounds (ATCAs) with the total content of 6.95%, 21 kinds of benzene carboxylic acid compounds (BCAs) with the total content of 25.44%, 23 kinds of hydrocarbon alkyl compounds (HCs) with the total content of 13.85%, 15 kinds of other compounds (OCs) with the total content of 6.83%, and 6 kinds of heteroatomic compounds with the total content of 1.22%, and the total yield of coal acid reaches 78.10%, wherein the yield of benzene carboxylic acid reaches 25.44%.

Embodiment 4

The process comprises the following steps: pulverizing Shengli lignite to 200 meshes or less, drying a pulverized coal sample at a temperature of 80° C. in vacuum for 10 h, weighing 0.5 g of the treated coal sample, sequentially adding 10 ml of acetic acid, 0.5 mmol of N-hydroxy-N-methylbenzamide and 0.2 mmol of iron acetate into a round-bottom flask, connecting a tee joint to an upper orifice of a condenser pipe, replacing oxygen in vacuum for three times so that the round-bottom flask is filled with the oxygen, keeping the oxygen pressure at 0.1 MPa, reacting at a temperature of 90° C. for 11 h, and observing the reaction conditions; filtering after the reaction is finished; decompressing a filtrate to remove the acetic acid, adding a small amount of ethyl acetate to dissolve, then adding an excess $CH_2N_2$/ether solution to esterify at room temperature for 10 h, using 0.45 μm filter paper to filter, and analyzing an esterified product through GC/MS.

A total of 123 compounds are identified by analyzing and detecting the distribution of oxidation products through an Agilent 7890/5975 gas chromatography-mass spectrometer, including 40 kinds of monocarboxylic acid compounds (MCAs) with the total content of 30.85%, 14 kinds of dicarboxylic acid compounds (DCAs) with the total content of 18.34%, 4 kinds of tricarboxylic acid compounds (ATCAs) with the total content of 3.83%, 21 kinds of benzene carboxylic acid compounds (BCAs) with the total content of 25.76%, 23 kinds of hydrocarbon alkyl compounds (HCs) with the total content of 12.15%, 15 kinds of other compounds (OCs) with the total content of 6.95%, and 6 kinds of heteroatomic compounds with the total content of 2.12%, and the total yield of coal acid reaches 78.78%, wherein the yield of benzene carboxylic acid reaches 25.76%.

Embodiment 5

The process comprises the following steps: pulverizing Shengli lignite to 200 meshes or less, drying a pulverized coal sample at a temperature of 80° C. in vacuum for 10 h, weighing 0.5 g of the treated coal sample, sequentially adding 10 ml of acetic acid, 0.5 mmol of 3,5-dinitro-N-hydroxy-N-methylbenzamide and 0.15 mmol of cobalt acetate into a round-bottom flask, connecting a tee joint to an upper orifice of a condenser pipe, replacing oxygen in vacuum for three times so that the round-bottom flask is filled with the oxygen, keeping the oxygen pressure at 0.1 MPa, reacting at a temperature of 110° C. for 9 h, and observing the reaction conditions; filtering after the reaction is finished; decompressing a filtrate to remove the acetic acid, adding a small amount of ethyl acetate to dissolve, then adding an excess $CH_2N_2$/ether solution to esterify at room temperature for 10 h, using 0.45 μm filter paper to filter, and analyzing an esterified product through GC/MS.

A total of 123 compounds are identified by analyzing and detecting the distribution of oxidation products through an Agilent 7890/5975 gas chromatography-mass spectrometer, including 40 kinds of monocarboxylic acid compounds (MCAs) with the total content of 36.08%, 14 kinds of dicarboxylic acid compounds (DCAs) with the total content of 15.76%, 4 kinds of tricarboxylic acid compounds (ATCAs) with the total content of 4.78%, 21 kinds of benzene carboxylic acid compounds (BCAs) with the total content of 28.85%, 23 kinds of hydrocarbon alkyl compounds (HCs) with the total content of 7.62%, 15 kinds of other compounds (OCs) with the total content of 5.05%, and 6 kinds of heteroatomic compounds with the total content of 1.86%, and the total yield of coal acid reaches 85.47%, wherein the yield of benzene carboxylic acid reaches 28.85%.

Embodiment 6

The process comprises the following steps: pulverizing Shengli lignite to 200 meshes or less, drying a pulverized coal sample at a temperature of 80° C. in vacuum for 10 h, weighing 0.5 g of the treated coal sample, sequentially adding 10 ml of acetic acid, 0.5 mmol of 1-hydroxy-2,2-diphenyl-3-indolone and 0.15 mmol of cobalt acetate into a round-bottom flask, connecting a tee joint to an upper orifice of a condenser pipe, replacing oxygen in vacuum for three times so that the round-bottom flask is filled with the oxygen, keeping the oxygen pressure at 0.1 MPa, reacting at a temperature of 100° C. for 10 h, and observing the reaction conditions; filtering after the reaction is finished; decompressing a filtrate to remove the acetic acid, adding a small amount of ethyl acetate to dissolve, then adding an excess $CH_2N_2$/ether solution to esterify at room temperature for 10 h, using 0.45 μm filter paper to filter, and analyzing an esterified product through GC/MS.

A total of 123 compounds are identified by analyzing and detecting the distribution of oxidation products through an Agilent 7890/5975 gas chromatography-mass spectrometer, including 40 kinds of monocarboxylic acid compounds (MCAs) with the total content of 32.74%, 14 kinds of dicarboxylic acid compounds (DCAs) with the total content of 12.83%, 4 kinds of tricarboxylic acid compounds (ATCAs) with the total content of 5.85%, 21 kinds of benzene carboxylic acid compounds (BCAs) with the total content of 25.12%, 23 kinds of hydrocarbon alkyl compounds (HCs) with the total content of 9.13%, 15 kinds of other compounds (OCs) with the total content of 11.80%, and 6 kinds of heteroatomic compounds with the total content of 2.53%, and the total yield of coal acid reaches 76.54%, wherein the yield of benzene carboxylic acid reaches 25.12%.

What is claimed is:

1. A method of catalytic oxidation of a lignite using oxygen as an oxidant at atmospheric pressure for mildly oxidizing the lignite using the oxygen as the oxidant under the action of a N-hydroxy amide catalyst and a metal salt or a metal oxide cocatalyst, comprising:

pulverizing a lignite to 200 mesh or less;

drying the pulverized lignite at a temperature of 80° C. in vacuum for 10 h;

weighing 0.5 g of the dried lignite;

sequentially adding 10 ml of acetic acid, 0.5 mmol of the N-hydroxy amide catalyst, and 0.15-0.25 mmol of the metal salt or the metal oxide cocatalyst into a round-bottom flask, wherein the N-hydroxy amide catalyst is one of compounds consisting of N-hydroxy o-sulfonyl benzimide, N,N-dihydroxy pyromellitic diimide, 1,3,5-trihydroxyisocyanuric acid, N-hydroxy-N-methylbenzamide, 3,5-dinitro-N-hydroxy-N-methylbenzamide, and 1-hydroxy-2,2-diphenyl-3-indolone, wherein the structures of the compounds are as follows:

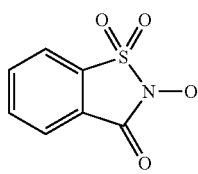
N-hydroxy o-sulfonyl benzimide

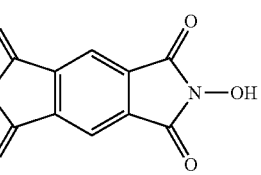
N,N-dihydroxy pyromellitic diimide

-continued

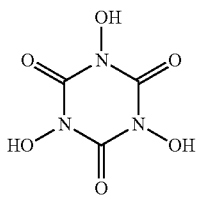
1,3,5-trihydroxyisocyanuric acid

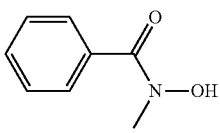
N-hydroxy-N-methylbenzamide

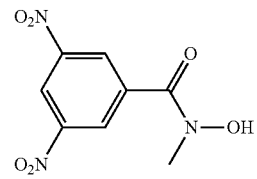
3,5-dinitro-N-hydroxy-N-methylbenzamide

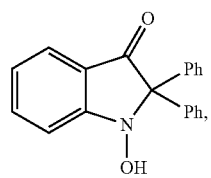
1-hydroxy-2,2-diphenyl-3-indolone and wherein the metal salt or the metal oxide cocatalyst is one of cobalt acetate, manganese acetate, copper acetate, iron acetate, and manganese dioxide;

connecting a tee joint to an upper orifice of a condenser pipe, replacing oxygen in vacuum for three times to fill the round-bottom flask with the oxygen and keeping the oxygen pressure at 0.1 MPa, and then reacting at a temperature of 80° C.-120° C. for 4-12 h and observing the reaction conditions;

using the oxygen as the oxidant to catalytically oxidize the lignite at an atmospheric pressure of 0.1 MPa;

filtering after the reaction is finished;

decompressing the filtrate to remove the acetic acid, adding a small amount of ethyl acetate to dissolve, and using an excess $CH_2N_2$/ether solution to esterify for 10 h at room temperature; and using a 0.45 μm filter paper to filter, and analyzing the esterified product through a gas chromatography-mass spectrometer.

2. The method of the catalytic oxidation of the lignite using oxygen as the oxidant at atmospheric pressure according to claim 1, wherein the amount of the lignite is 0.5 g, the amount of the N-hydroxy amide catalyst is 0.5 mmol, the amount of the metal salt or the metal oxide cocatalyst is 30%-50% of the amount of the N-hydroxy amide catalyst based on a molar ratio, and the total yield of a coal acid is 66.21%-85.47%, wherein the yield of a benzene carboxylic acid is 22.58%-28.85%.

* * * * *